US010067569B2

(12) United States Patent
Tarn et al.

(10) Patent No.: US 10,067,569 B2
(45) Date of Patent: Sep. 4, 2018

(54) TOUCHLESS INTERFACE FOR A MEDICAL TREATMENT SYSTEM

(71) Applicant: Fresenius Medical Care Holdings, Inc., Waltham, MA (US)

(72) Inventors: Jeffrey Tarn, Walnut Creek, CA (US); Fei Wang, Concord, CA (US); Lee Daniel Tanenbaum, Walnut Creek, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 34 days.

(21) Appl. No.: 14/826,513

(22) Filed: Aug. 14, 2015

(65) Prior Publication Data

US 2017/0045947 A1    Feb. 16, 2017

(51) Int. Cl.
*G09G 5/00*     (2006.01)
*G06F 3/01*     (2006.01)
(Continued)

(52) U.S. Cl.
CPC ............ *G06F 3/017* (2013.01); *A61M 1/1601* (2014.02); *G06F 3/005* (2013.01);
(Continued)

(58) Field of Classification Search
CPC ...... G06F 3/017; G06F 3/005; A61M 1/1601; A61M 2205/33; A61M 2205/502; H04N 5/247; H04N 5/2256
See application file for complete search history.

(56) References Cited

U.S. PATENT DOCUMENTS 7,078,911 B2    7/2006   Cehelnik
7,539,533 B2    5/2009   Tran
(Continued)

FOREIGN PATENT DOCUMENTS

DE    198 45 027 C2    4/2000
EP    2237131 A1       10/2010
(Continued)

OTHER PUBLICATIONS

Notification of Transmittal of the International Search Report and the Written Opinion of the International Searching Authority for corresponding PCT Application No. PCT/US2016/045113, dated Nov. 7, 2016, 11 pages.

*Primary Examiner* — Rodney Amadiz
(74) *Attorney, Agent, or Firm* — Fish & Richardson P.C.

(57) ABSTRACT

A dialysis machine comprising: one or more processing units configured to transmit control data; a pump configured to pump medical fluid to and from a patient based at least in part on control data received from the processing unit; an electronic panel comprising: a display surface, and at least one panel control unit configured to cause the electronic panel to display at least one user interface element that can be invoked by a user; at least one projector; and at least one camera; wherein the one or more processing units are configured to: process input received by the camera, determine a location of a physical object in a field of view of the camera based on the processed input, determine, based on processed input received on at least one occasion, that the location of the physical object represents an invocation of the at least one user interface element displayed on the electronic panel, and determine the control data based on the processed input.

13 Claims, 13 Drawing Sheets

(51) Int. Cl.
*A61M 1/16* (2006.01)
*G06F 3/00* (2006.01)
*H04N 5/225* (2006.01)
*H04N 5/247* (2006.01)
*G06F 19/00* (2018.01)
*G16H 40/63* (2018.01)

(52) U.S. Cl.
CPC ......... *G06F 19/3481* (2013.01); *G16H 40/63* (2018.01); *H04N 5/2256* (2013.01); *H04N 5/247* (2013.01); *A61M 2205/33* (2013.01); *A61M 2205/502* (2013.01)

(56) References Cited

U.S. PATENT DOCUMENTS

| | | |
|---|---|---|
| 8,487,881 B2 | 7/2013 | Keenan |
| 8,970,503 B2 | 3/2015 | Christie et al. |
| 2004/0193413 A1 | 9/2004 | Wilson et al. |
| 2006/0200260 A1 | 9/2006 | Hoffberg et al. |
| 2008/0114226 A1 | 5/2008 | Music et al. |
| 2009/0259960 A1 | 10/2009 | Steinle et al. |
| 2010/0066676 A1 | 3/2010 | Kramer et al. |
| 2011/0157480 A1 | 6/2011 | Curl |
| 2011/0163030 A1 | 7/2011 | Weaver et al. |
| 2011/0164163 A1 | 7/2011 | Bilbrey et al. |
| 2012/0194561 A1* | 8/2012 | Grossinger ............. G06F 3/017 345/661 |
| 2013/0018301 A1 | 1/2013 | Weaver et al. |
| 2013/0249855 A1 | 9/2013 | Zhang |
| 2013/0257748 A1 | 10/2013 | Ambrus et al. |
| 2014/0104168 A1 | 4/2014 | Hegde |
| 2014/0266983 A1 | 9/2014 | Christensen |
| 2014/0267003 A1 | 9/2014 | Wang et al. |
| 2014/0306912 A1* | 10/2014 | Woolley ................ G06F 3/0418 345/173 |
| 2015/0199824 A1* | 7/2015 | Kim ..................... G06T 7/2033 382/103 |
| 2015/0253860 A1 | 9/2015 | Merics et al. |

FOREIGN PATENT DOCUMENTS

| | | |
|---|---|---|
| EP | 2857053 A1 | 4/2015 |
| WO | WO 2008/042219 A2 | 4/2008 |
| WO | WO2015134229 A1 | 9/2015 |

\* cited by examiner

TOUCHLESS INTERFACE FOR A MEDICAL TREATMENT SYSTEM

TECHNICAL FIELD

This disclosure relates to an input device (e.g., a display) for a medical treatment system.

BACKGROUND

Dialysis is a treatment used to support a patient with insufficient renal function. Dialysis machines typically include input devices that can be used by nurses or doctors to input information related to treatment into the dialysis machine.

SUMMARY

In one aspect, a dialysis machine includes one or more processing units configured to transmit control data. The dialysis machine also includes a pump configured to pump medical fluid to and from a patient based at least in part on control data received from the processing unit. The dialysis machine also includes an electronic panel. The electronic panel includes a display surface and at least one panel control unit configured to cause the electronic panel to display at least one user interface element that can be invoked by a user. The dialysis machine also includes at least one projector and at least one camera. The one or more processing units are configured to process input received by the camera. The one or more processing units are also configured to determine a location of a physical object in a field of view of the camera based on the processed input. The one or more processing units are also configured to determine, based on processed input received on at least one occasion, that the location of the physical object represents an invocation of the at least one user interface element displayed on the electronic panel. The one or more processing units are also configured to determine the control data based on the processed input.

Implementations can include one or more of the following features.

In some implementations, the projector includes a device that emits light.

In some implementations, the input received by the camera includes an image of pixels. Each pixel is defined by at least a u-coordinate value representing a horizontal position and a v-coordinate value representing a vertical position.

In some implementations, the position of the physical object is determined based on the u-coordinate value and the v-coordinate value of a pixel of the image.

In some implementations, the position of the physical object is determined by calculating an x-coordinate value, a y-coordinate value, and a z-coordinate value. The x, y, and z-coordinate values are each determined based on one or more of the following: the u-coordinate value, the v-coordinate value, a focal length of the camera in pixels, and a distance between the projector and the camera.

In some implementations, the at least one processor is configured to determine that the physical object is a physical object of interest.

In some implementations, the physical object is determined to be a physical object of interest based at least in part on a width of the physical object.

In some implementations, the physical object of interest is a finger of a human hand.

In some implementations, the projector emits a line. The length of the line depends on a distance between a point in space and the projector.

In some implementations, the dialysis machine includes four projectors and four cameras. A first projector is positioned above the electronic panel, a second projector is positioned below the electronic panel, a third projector is positioned to a left side of the electronic panel, and a fourth projector is positioned to a right side of the electronic panel.

In another aspect, a method performed by one or more processors of a dialysis machine includes processing visual input. The method also includes determining a location of a physical object based on the processed visual input. The method also includes determining, based on processed visual input received on at least one occasion, that the location of the physical object represents an invocation of at least one invokable user interface element displayed by an electronic panel of the dialysis machine.

Implementations can include one or more of the following features.

In some implementations, the visual input includes information related to a light that is projected onto the physical object.

In some implementations, the light includes infrared light.

In some implementations, the visual input includes an image of pixels. Each pixel is defined by at least a u-coordinate value representing a horizontal position and a v-coordinate value representing a vertical position.

In some implementations, the position of the physical object is determined based on the u-coordinate value and the v-coordinate value of a pixel of the image.

In some implementations, the position of the physical object is determined by calculating an x-coordinate value, a y-coordinate value, and a z-coordinate value. The x, y, and z-coordinate values are each determined based on one or more of the following: the u-coordinate value, the v-coordinate value, a focal length, in pixels, of a camera that processes the visual input, and a distance between the camera and a projector that emits a light that is projected onto the physical object.

In some implementations, the method also includes determining that the physical object is a physical object of interest.

In some implementations, the physical object is determined to be a physical object of interest based at least in part on a width of the physical object.

In some implementations, the physical object of interest is a finger of a human hand.

In another aspect, a non-transitory computer-readable medium stores software that, when executed by one or more processors, performs a method including processing visual input. The method also includes determining a location of a physical object based on the processed visual input. The method also includes determining, based on processed visual input received on at least one occasion, that the location of the physical object represents an invocation of at least one invokable user interface element displayed by an electronic panel of a dialysis machine.

Implementations can include one or more of the following advantages.

In some implementations, the devices and techniques described herein can promote cleanliness and sterilization in a dialysis environment, thereby reducing the risk of facilitating the spread of infection and eliminating the need for the user to wear gloves. Cleanliness and sterilization can be especially important in a medical environment due to the fragile health of the patients. The touchless nature of the devices and techniques allow for a user to interact with the dialysis machine without touching the machine.

In some implementations, the electronic panel is configured to receive multiple inputs from the user. The multiple inputs may be received at different times (e.g., a gesture), or may be concurrent (e.g., multi-gesture input). The capability to receive multiple inputs from the user increases the number of distinct interactions that the user can have with the display 118, thereby increasing the level of control that the user has over the dialysis machine.

Other aspects, features, and advantages of the invention will be apparent from the description and drawings, and from the claims.

DESCRIPTION OF DRAWINGS

FIG. 3b is an example of an image that is constructed by a camera based on the position of the object in FIG. 3a.

DETAILED DESCRIPTION

Figure 1:
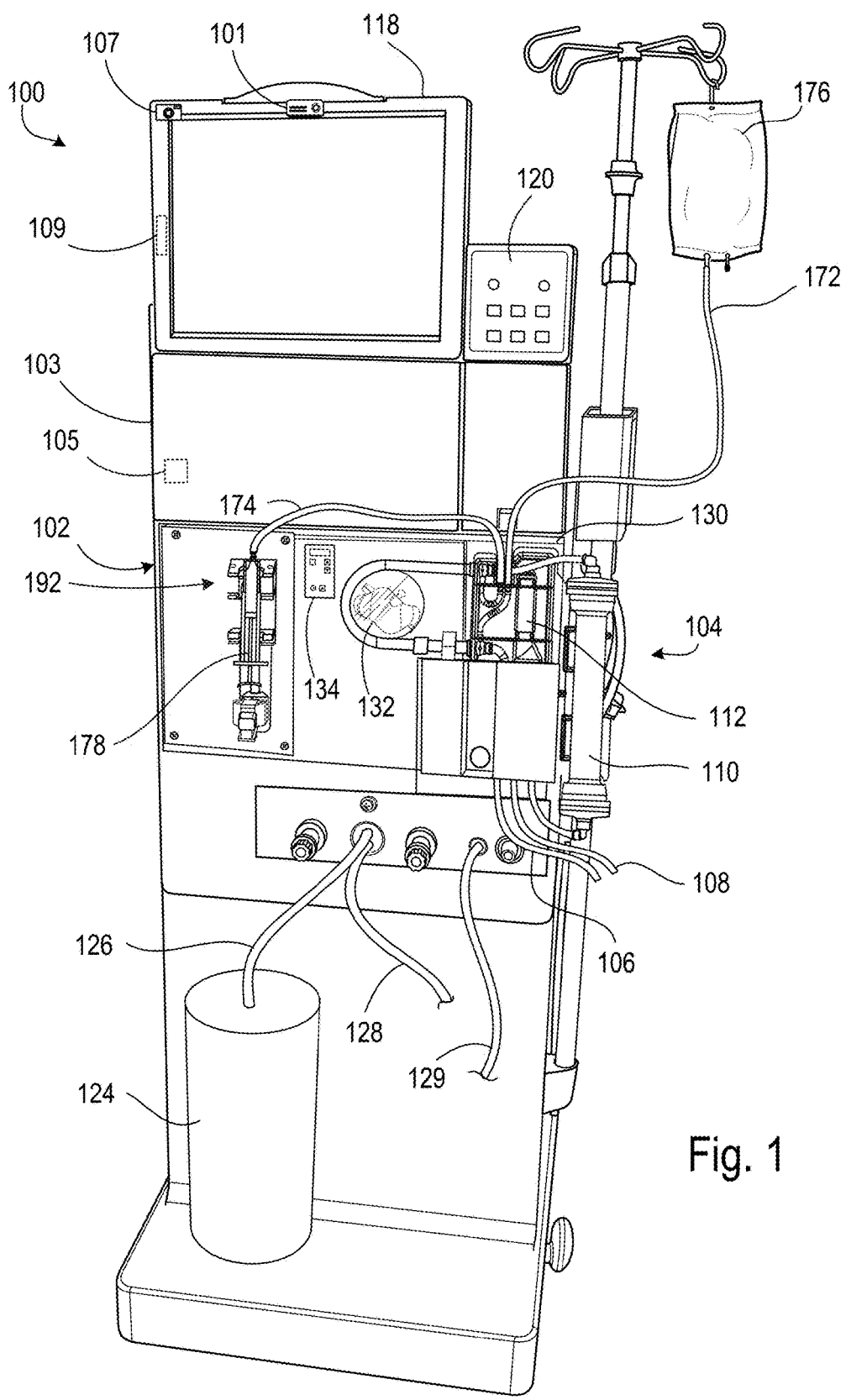
FIG. 1 is a front perspective view of a hemodialysis system, including a display with a touchless interface.

At various points before, during, or after a medical fluid treatment such as a dialysis treatment, medical personnel may need to input information into a dialysis machine. For example, before treatment, a nurse may input patient parameters, such as a Patient ID. The nurse may also input medical treatment information, such as information related to the patient's treatment prescription.

The medical fluid treatment systems (e.g., dialysis systems) described herein can include an input device with a non-contact (e.g., touchless) interface for receiving input from a user. In some examples, the dialysis machine includes a display, a camera, a projector, and a processor. The display is configured to display user interface elements, such as user interface buttons, that can be invoked by a user without the user making contact with the display. Based on input received by the camera, the processor can determine a location of a finger of the user's hand in a field of view of the camera. The processor can also determine that the location of the finger represents an invocation of a particular user interface element that is being displayed.

In some examples, the user's finger may be positioned in a space in front of the display. The projector is configured to emit an infrared light in a plane that runs through the space in front of the display. When the user's finger intersects the plane of infrared light, an infrared line segment is projected onto the user's finger. The camera detects the infrared line segment that is projected onto the user's finger and constructs an image that includes a representation of the infrared line segment in pixels. The image may be two-dimensional and have a coordinate system wherein a u-coordinate represents a horizontal position of a pixel and a v-coordinate represents a vertical position of a pixel. In this way, a pixel can be characterized by a value (e.g., a numerical value) representing the u-coordinate and a value representing the v-coordinate.

The processor receives and processes the information received from the camera to determine whether the location of the finger represents an invocation of a particular user interface element. For example, the processor receives information related to the image constructed by the camera and determines that a physical object is positioned in a particular space in front of the display.

As a preliminary step, the processor may determine whether the physical object (e.g., the finger) is a physical object of interest. Such a determination may be based on a width of the finger, which may be determined based on the length of the infrared line segment projected on the finger.

If the finger is determined to be a physical object of interest, the processor determines the location of the finger in reference to the display (e.g., in terms of x, y, z-coordinates). The location of the finger is determined based at least in part on the image constructed by the camera, the u and v-coordinates of the infrared line segment, the position of the camera, the position of the projector, the projection angle of the projector relative to the display, and the focal length of the camera. The focal length of the camera is a measure of how strongly the system converges or diverges light, and corresponds to dimensions of objects that appear in the image constructed by the camera. An object within the camera's field of view tends to be in focus if the object is located at a distance from the lens that is close to the focal length. A longer focal length tends to correspond to a narrower angle of view, while a shorter focal length tends to correspond to a wider angle of view.

The location of the finger can be determined according to the following equations:

$$x = \frac{b}{f * \cot(\theta) - u} * u$$

$$y = \frac{b}{f * \cot(\theta) - u} * v$$

$$z = \frac{b}{f * \cot(\theta) - u} * f$$

Once the x, y, z-coordinates of the finger are determined, the processor determines whether the location of the finger represents an invocation of a particular user element. The processor identifies a position on the display that is normal to the x, y, z-coordinates of the finger. If the identified position corresponds to a user interface element, the processor determines that the particular user interface element is being invoked. The dialysis machine may perform one or more actions based on the user interface element being invoked.

Use of the non-contact input device can promote cleanliness and sterilization in a dialysis environment, thereby reducing the risk of facilitating the spread of infection and eliminating the need for the user to wear gloves. Cleanliness and sterilization can be especially important in a medical environment due to the fragile health of the patients. The touchless nature of the input device allows for the user to interact with the dialysis machine without making physical contact with the machine.

Referring to FIG. 1, a hemodialysis system 100 includes a hemodialysis machine 102 to which a disposable blood component set 104 that forms a blood circuit is connected. As described below, the hemodialysis system 100 includes an input device such as an electronic panel (e.g., a display 118).

In general, during hemodialysis, arterial and venous patient lines 106, 108 of the blood component set 104 are connected to a patient and blood is circulated through various blood lines and components, including a dialyzer 110, of the blood component set 104. At the same time, dialysate is circulated through a dialysate circuit formed by the dialyzer 110 and various other dialysate components and dialysate lines connected to the hemodialysis machine 102. Many of these dialysate components and dialysate lines are located inside the housing 103 of the hemodialysis machine 102, and are thus not visible in FIG. 1. The dialysate passes through the dialyzer 110 along with the blood. The blood and dialysate passing through the dialyzer 110 are separated from one another by a semi-permeable structure (e.g., a semi-permeable membrane and/or semi-permeable microtubes) of the dialyzer 110. As a result of this arrangement, toxins are removed from the patient's blood and collected in the dialysate. The filtered blood exiting the dialyzer 110 is returned to the patient. The dialysate that exits the dialyzer 110 includes toxins removed from the blood and is commonly referred to as "spent dialysate." The spent dialysate is routed from the dialyzer 110 to a drain.

One of the components of the blood component set 104 is an air release device 112. The air release device 112 includes a self-sealing vent assembly that allows air to pass therethrough while inhibiting (e.g., preventing) liquid from passing therethrough. As a result, if blood passing through the blood circuit during treatment contains air, the air will be vented to atmosphere as the blood passes through the air release device 112.

As shown in FIG. 1, a dialysate container 124 is connected to the hemodialysis machine 102 via a dialysate supply line 126. A drain line 128 and an ultrafiltration line 129 also extend from the hemodialysis machine 102. The dialysate supply line 126, the drain line 128, and the ultrafiltration line 129 are fluidly connected to the various dialysate components and dialysate lines inside the housing 103 of the hemodialysis machine 102 that form part of the dialysate circuit. During hemodialysis, the dialysate supply line 126 carries fresh dialysate from the dialysate container 124 to the portion of the dialysate circuit located inside the hemodialysis machine 102. As noted above, the fresh dialysate is circulated through various dialysate lines and dialysate components, including the dialyzer 110, that form the dialysate circuit. As the dialysate passes through the dialyzer 110, it collects toxins from the patient's blood. The resulting spent dialysate is carried from the dialysate circuit to a drain via the drain line 128. When ultrafiltration is performed during treatment, a combination of the spent dialysate and excess fluid drawn from the patient is carried to the drain via the ultrafiltration line 129.

The blood component set 104 is secured to a module 130 attached to the front of the hemodialysis machine 102. The module 130 includes a blood pump 132 capable of driving blood through the blood circuit. The module 130 also includes various other instruments capable of monitoring the blood flowing through the blood circuit. The module 130 includes a door that when closed, as shown in FIG. 1, cooperates with the front face of the module 130 to form a compartment sized and shaped to receive the blood component set 104. In the closed position, the door presses certain blood components of the blood component set 104 against corresponding instruments exposed on the front face of the module 130. As will be described in greater detail below, this arrangement facilitates control of the flow of blood through the blood circuit and monitoring of the blood flowing through the blood circuit.

The blood pump 132 can be controlled by a blood pump module 134. The blood pump module 134 includes a display window, a start/stop key, an up key, a down key, a level adjust key, and an arterial pressure port. The display window displays the blood flow rate setting during blood pump operation. The start/stop key starts and stops the blood pump 132. The up and down keys increase and decrease the speed of the blood pump 132. The level adjust key raises a level of fluid in an arterial drip chamber.

A drug pump 192 also extends from the front of the hemodialysis machine 102. The drug pump 192 is a syringe pump that includes a clamping mechanism configured to retain a syringe 178 of the blood component set 104. The drug pump 192 also includes a stepper motor configured to move the plunger of the syringe 178 along the axis of the syringe 178. A shaft of the stepper motor is secured to the plunger in a manner such that when the stepper motor is operated in a first direction, the shaft forces the plunger into the syringe, and when operated in a second direction, the shaft pulls the plunger out of the syringe 178. The drug pump 192 can thus be used to inject a liquid drug (e.g., heparin) from the syringe 178 into the blood circuit via a drug delivery line 174 during use, or to draw liquid from the blood circuit into the syringe 178 via the drug delivery line 174 during use.

Still referring to FIG. 1, the hemodialysis machine 102 includes a display 118 and a control panel 120. The display 118 has a non-contact (e.g., touchless) interface for receiving input from a user. The display 118 and the control panel 120 allow the operator to input data, e.g., various different treatment parameters, to the hemodialysis machine 102 and to control the hemodialysis machine 102. In addition, the display 118 conveys information to the operator of the hemodialysis system 100.

The hemodialysis machine 102 includes one or more processing units configured to transmit control data (e.g., data that causes the dialysis machine 102 to perform one or more dialysis functions). In this example, the hemodialysis machine 102 includes a control unit 105 (e.g., a processor such as a microprocessor or microcontroller) that resides inside the machine and which is configured to transmit control data, communicate with the display 118 and the control panel 120, and cause the hemodialysis machine 102 to carry out dialysis functions (e.g., starting or stopping a pump of the dialysis machine 102). The control unit 105 is configured to receive data from the display 118 and the control panel 120 and control the hemodialysis machine 102 based on the received data, as described in more detail below. The hemodialysis machine 102 also includes a panel control unit 109 (e.g., a processor such as a microprocessor or microcontroller) that is configured to cause the display 118 to display one or more user interface elements that can be invoked by a user without the user making contact with the display 118.

The hemodialysis machine 102 includes a projector 101 and a camera 107 that are affixed to the display 118. The projector 101 is configured to emit a light (e.g., an infrared light) in a plane that runs through a space in front of the display 118. If an object is present in the plane, the light is projected on the object. The camera 107 is configured to detect the light that is projected on the object and construct an image that includes a representation of the infrared line segment, as described in more detail below.

Although FIG. 1 is described in connection with a hemodialysis machine, it is specifically noted that the system and techniques described herein may be used with other types of dialysis and machines therefor, including peritoneal dialysis (PD).

Figure 2A:
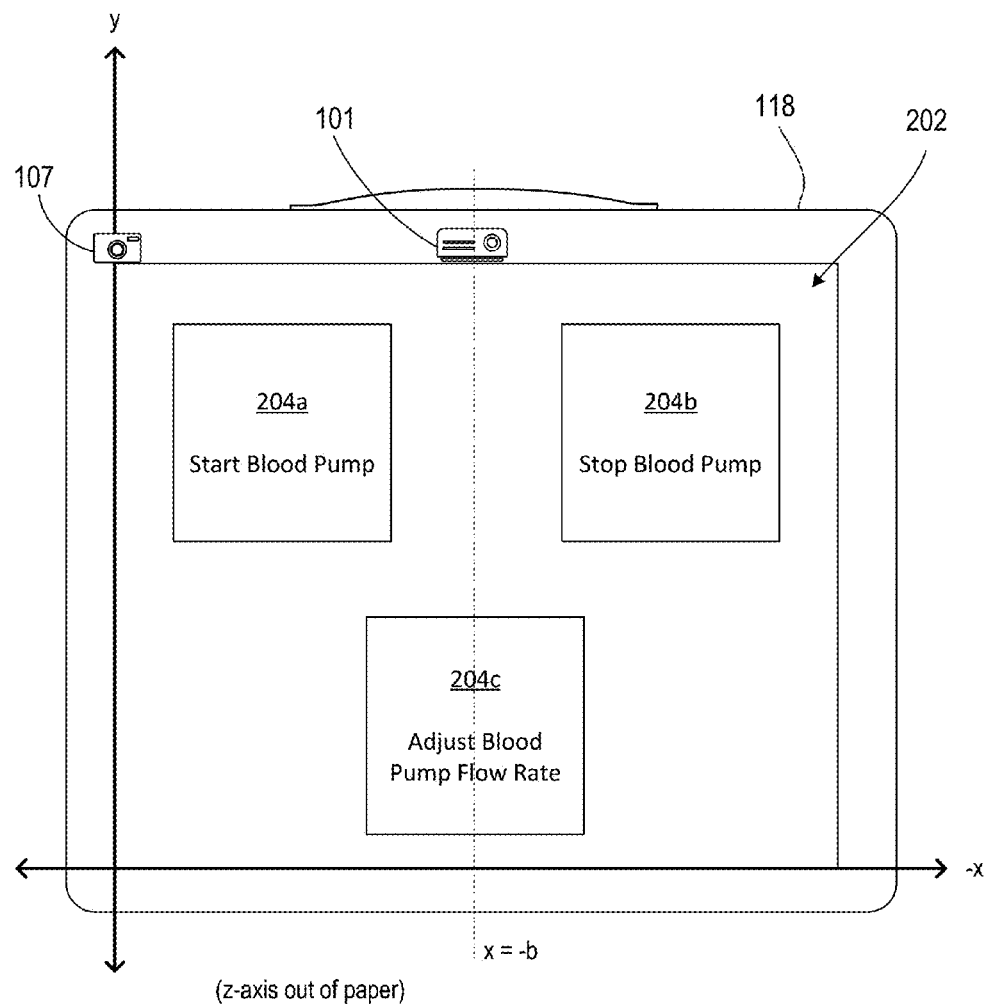
FIG. 2a is a front-facing view of the display of FIG. 1.

FIG. 2a shows an example of the electronic panel (e.g., the display 118). The display 118 includes a display surface 202 and a panel control unit (109 of FIG. 1). The display 118 presents one or more user interface elements 204a-c. In this example, the user interface elements 204a-c are buttons that can be invoked by the user.

A three-dimensional coordinate system (210 of FIG. 2b) is associated with the display 118. The coordinate system includes an x-axis, a y-axis, and a z-axis. The z-axis runs out of the paper/screen, and thus is not shown in FIG. 2a. The coordinate system has an origin at the bottom-left corner of the display 118. The camera 107 is positioned along the y-axis at approximately x=0. In this example, the x-axis is represented such that negative values of x appear to the right, and positive values of x appear to the left. The projector 101 is positioned at x=−b and at approximately the same y value as the camera 107.

Figure 2B:
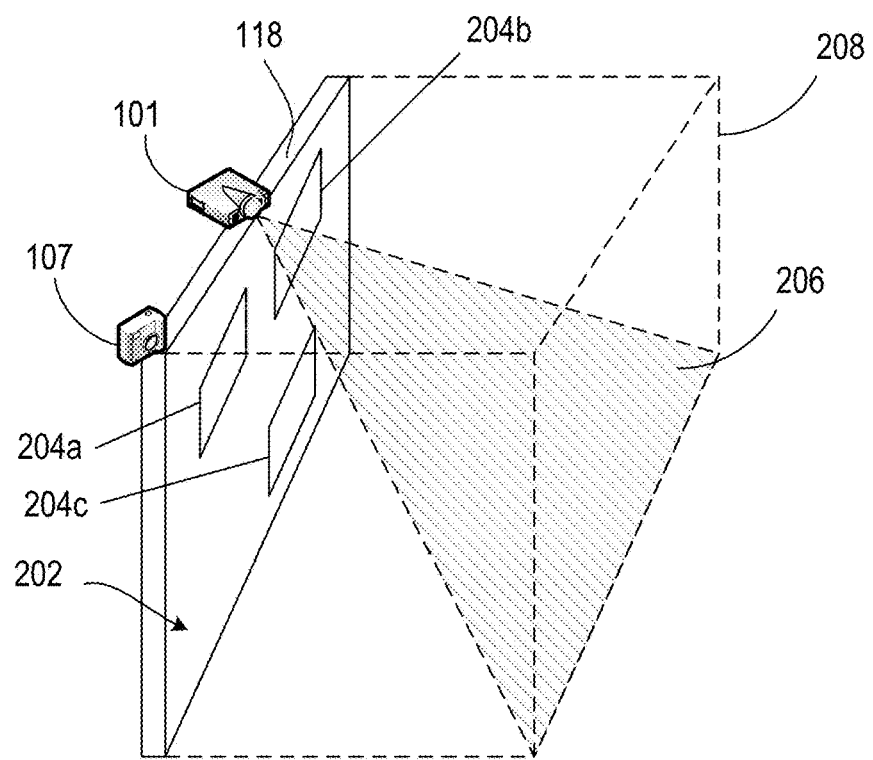
FIG. 2b is a perspective view of the display.
Figure 2B:
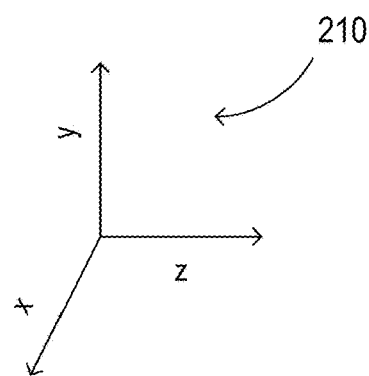

FIG. 2b shows a perspective view of the display 118 of FIG. 2a in reference to a three-dimensional coordinate system 210. The projector 101 is positioned such that the projector 101 emits the infrared light in a particular plane 206 that runs through a space 208 (e.g., a three-dimensional area, sometimes referred to as a volume) in front of the display 118. In this example, the projector 101 is tilted downwards. As such, the light is emitted away from the display in a downwards diagonal manner, starting at the top of the display 118 and running through the space 208. The space 208 in front of the display 118 is represented by the dash-lined rectangular prism shown in FIG. 2b. When an object (e.g., the user's finger) intersects the plane 206, the infrared light is projected onto the object.

Figure 3A:
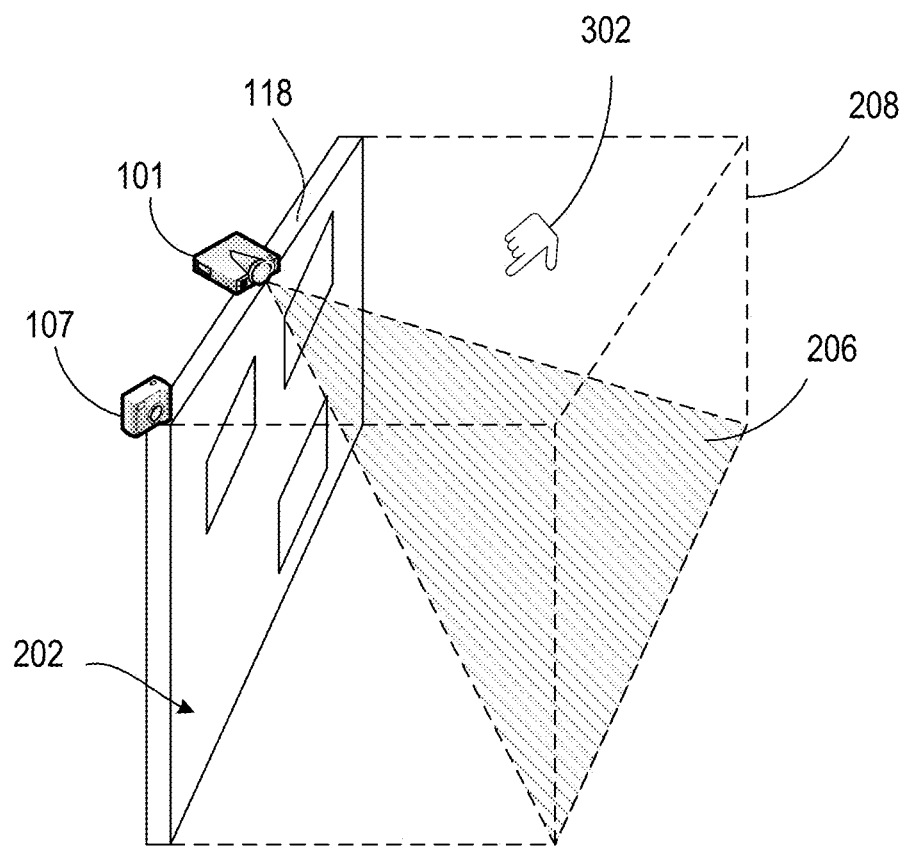
FIG. 3a is a perspective view of the display in which an object is positioned in a space in front of the display.
Figure 3A:
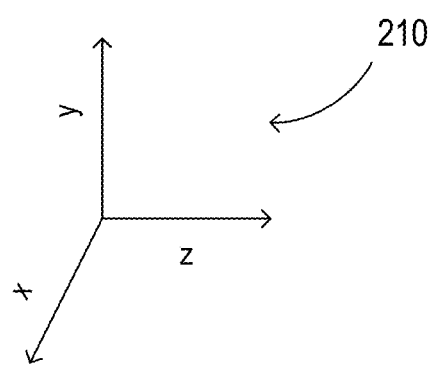

FIG. 3a shows a perspective view of the display 118 of FIGS. 2a and 2b in which a user's finger 302 is not intersecting the plane 206. Although the user's finger 302 is positioned within the space 208 in front of the display 118, the user's finger 302 is not in a position at which the projector 101 emits light. As described in more detail below, the hemodialysis system 100 can include additional projectors that emit light in additional planes that run through the space 208 in front of the display 118. The inclusion of additional projectors can increase the number of positions within the space 208 in front of the display 118 at which the user's finger 302 can be detected (e.g., by intersecting one of the additional planes of light).

Figure 3B:
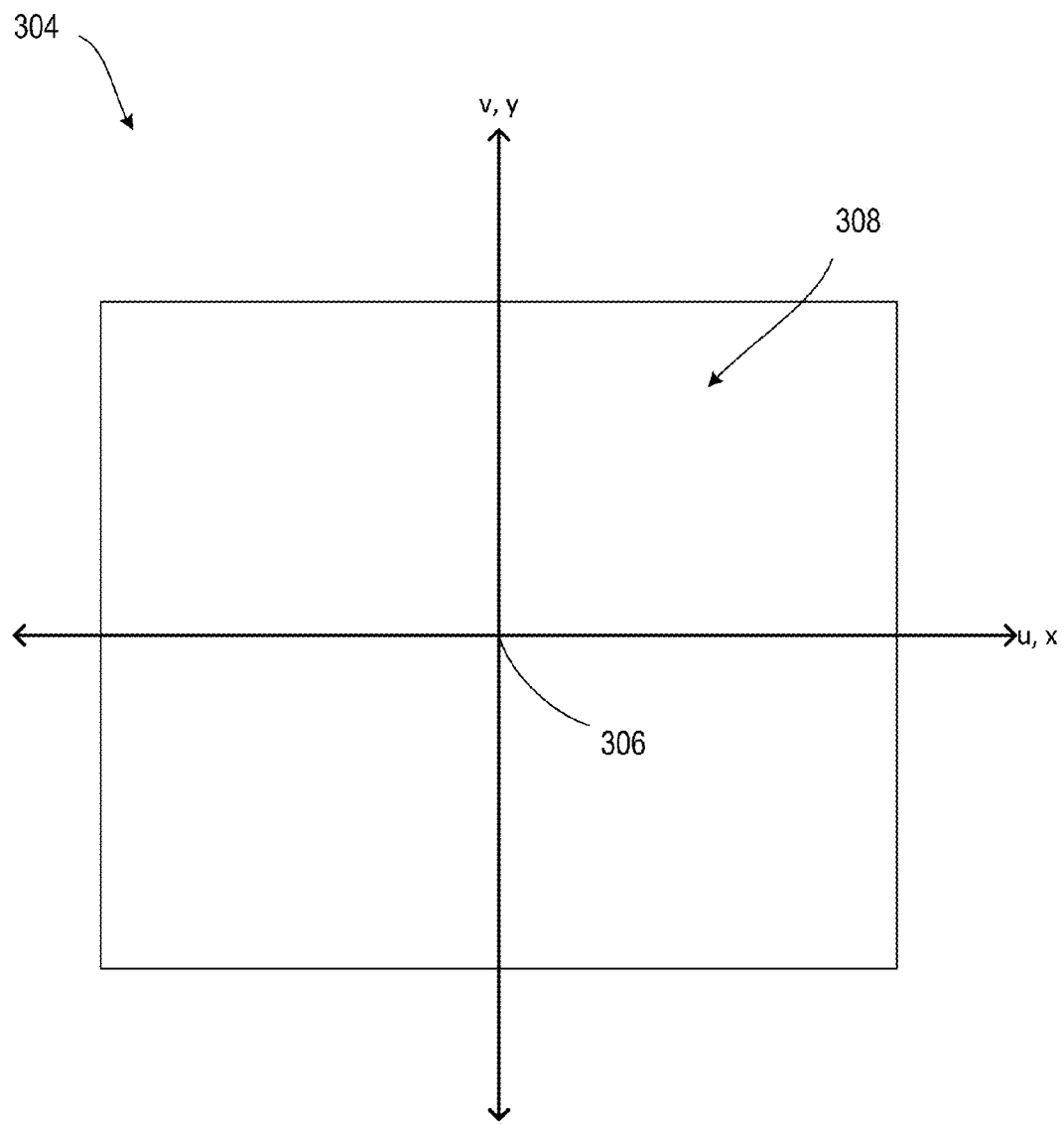

FIG. 3b shows an example of an image 304 that is constructed by the camera 107 based on the position of the user's finger 302 in FIG. 3a. The image 304 is associated with a coordinate system in which a u-coordinate value represents a horizontal position of a pixel and a v-coordinate value represents a vertical position of a pixel. An origin 306 of the image 304 corresponds to the x, y position of the camera 107. More specifically, the origin 306 corresponds to a center of a lens of the camera 107. In this example, because the camera 107 is positioned at the top-left corner of the display 118, one quadrant of the image 304 has u, v-coordinate values that correspond to x, y-coordinate values that are within the space 208 in front of the display 118. The quadrant is the top-right quadrant 308 of the image 304. The top-right quadrant 308 of the image 304 is the quadrant that has u, v-coordinate values that correspond to x, y-coordinate values that are within the space 208 due to the mirror nature of camera images. In other words, from the camera's 107 front-facing perspective, the space 208 is located to the bottom-left of the camera 107, but in the image 304 that is constructed by the camera 107, the top-right quadrant 308 corresponds to the coordinates of the space 208. If an object were to intersect the plane (206 of FIG. 3a), the camera 107 would detect the projected infrared light, and the representation of the infrared line segment would appear in the top-right quadrant 308 of the image 304. However, in this example, the user's finger 302 is not intersecting the plane 206. Therefore, the image 300 is substantially blank (e.g., it does not include a representation of the infrared line segment).

Figure 3C:
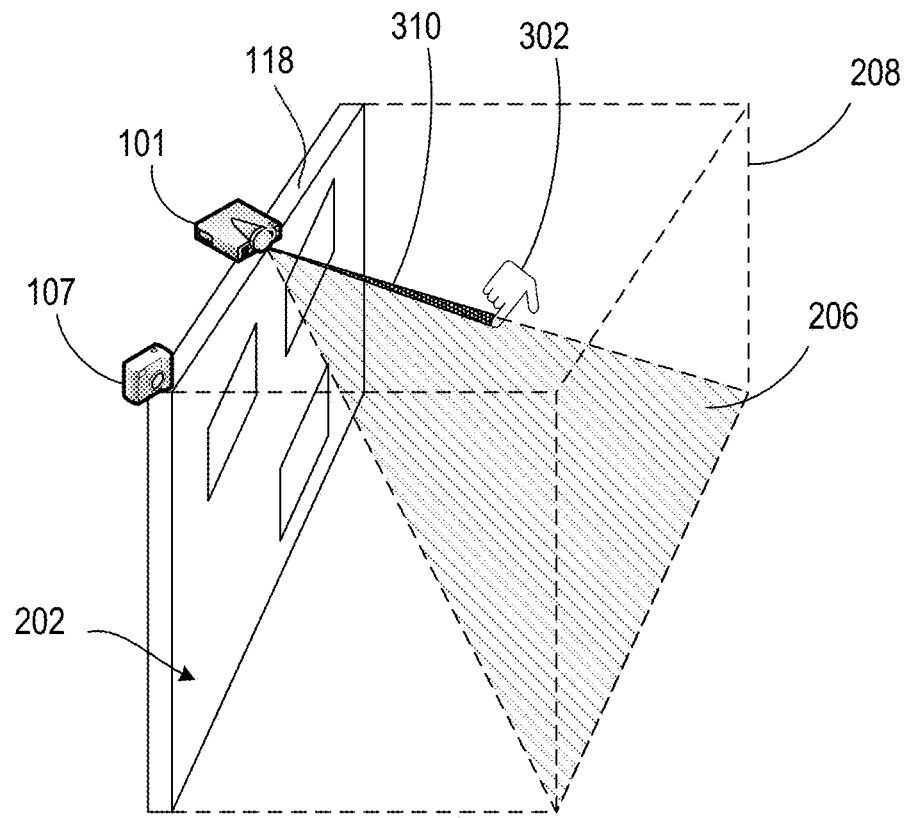
FIG. 3c is a perspective view of the display of FIG. 3a in which the object is intersecting a plane of light emitted from a projector.

FIG. 3c shows a perspective view of the display 118 of FIGS. 2a and 2b in which the user's finger 302 is intersecting the plane 206 of emitted infrared light. The position of the user's finger 302 causes a portion 310 of the infrared light emitted by the projector 101 to be projected onto the user's finger 302.

Figure 3D:
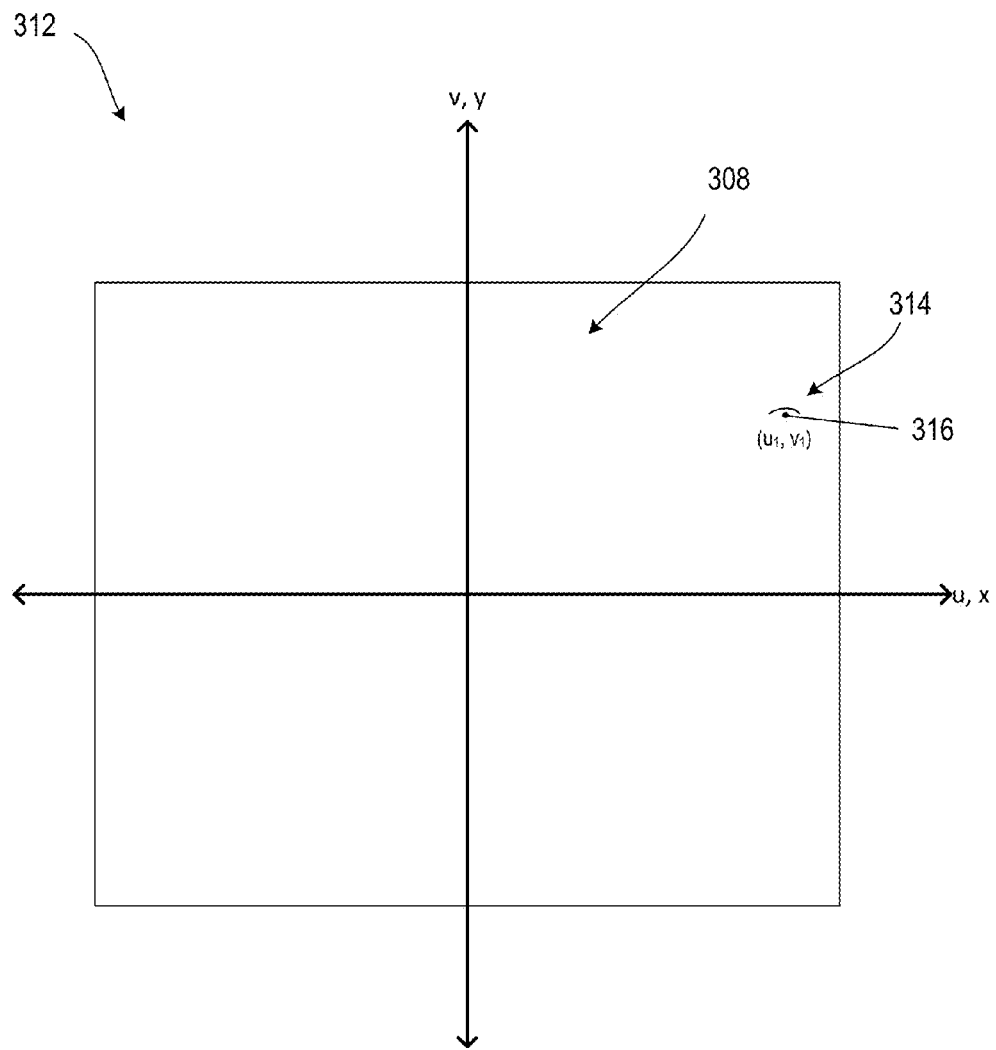
FIG. 3d is an example of an image that is constructed by the camera based on the position of the object in FIG. 3c.

As described above, the camera 107 detects the infrared light that is projected onto the user's finger 302 and constructs an image that includes a representation of the infrared light. FIG. 3d shows an example of an image 312 that is constructed by the camera 107 based on the position of the user's finger 302 in FIG. 3c. The representation of the infrared light appears as a segment 314 of pixels. The segment 314 is curved because the surface of the user's finger 302 is rounded.

In some implementations, the control unit (105 of FIG. 1) may determine whether the object that is represented by the segment 314 is a physical object of interest before proceeding with further processing. Such a determination may be based on a width of the 314 segment. For example, if the width of a segment is greater than a threshold (e.g., a predetermined threshold), the control unit 105 may determine that the object that caused the segment to be generated was likely not a finger of a user, and thus may identify the segment as an unintended or inappropriate input and choose to ignore the segment.

The threshold is predetermined if it is based on data that is available to the hemodialysis system 100 when a user starts using the non-contact interface at a particular time. In some implementations, the threshold may be based on data stored on and/or by the hemodialysis system 100, such as configuration data that is stored at the time of manufacture. In some implementations, the data may be based on one or more calibrations of the hemodialysis system 100. For example, the threshold may be determined by a calibration involving the user's finger, and the threshold may be subsequently modified based on additional calibrations.

The control unit 105 may determine an object location image point 316 based on the segment 314. In the examples shown in the figures, the control unit 105 is a separate unit from the panel control unit 109. As described above, the panel control unit 109 is configured to cause the display 118 to display the one or more user interface elements 204a-c.

The control unit 105 is responsible for, among other things, causing the hemodialysis machine 102 to carry out dialysis functions. Because the control unit 105 and the panel control unit 109 can be separate, isolated processors, a user interface malfunction involving the panel control unit 109 will not affect the dialysis functions carried out by the control unit 105, thereby reducing the risk of the patient encountering an unsafe condition.

In some implementations, the control unit 105 may average the coordinate values of each pixel in the segment 314 to determine an average (e.g., mean) coordinate value of the segment 314. The control unit 105 may then assign the average coordinate value to the object location image point 316. Representing the segment 314 as a single object location image point 316 can simplify subsequent processing of information related to the image 312. In this example, the object location image point 316 has coordinate values $u_1$, $v_1$ in the image 312.

Figure 4:
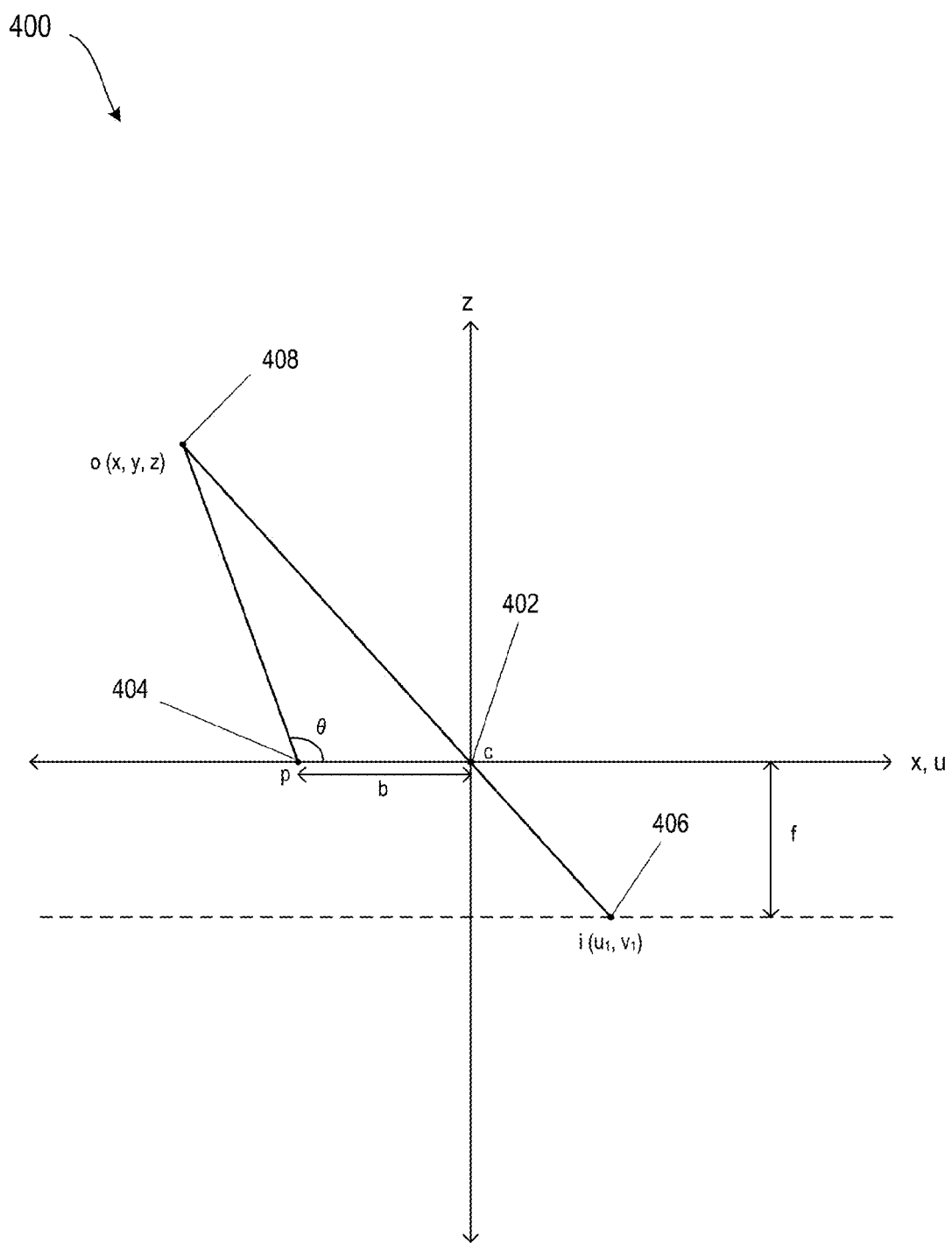
FIG. 4 is an example of a coordinate system that illustrates how the position of the object in FIG. 3c is determined.

Once the u, v-coordinate values of the object location image point 316 are known, the control unit 105 can determine the x, y, z-coordinate values of a point that corresponds to the location of the user's finger 302 within the space 208 in front of the display 118. FIG. 4 shows an example of a coordinate system 400 that illustrates now the x, y, z-coordinate values of the point are determined. The coordinate system 400 includes the three-dimensional coordinate system 210 of FIGS. 2a, 2b, 3a, and 3c, as well as the u, v-coordinate system described with reference to FIGS. 3b and 3d. The origin 402 of the coordinate system 400 corresponds to the location of the camera 107. The origin 402 is represented as point c.

The x and u values are represented on one axis. Briefly referring back to FIGS. 2a and 2b, negative values of x represent positions that may be located directly in front of the display 118, and positive values of x represent positions that are not located directly in front of the display 118. This is due to the x-axis of the coordinate system 210 being defined as it is, e.g., such that positive x values correspond to locations that are not in front of the display 118. Briefly referring back to FIGS. 3b and 3d, positive values of u represent positions in the image that may correspond to locations that are directly in front of the display 118, and negative values of u represent positions in the image that do not correspond to locations that are directly in front of the display 118.

The y and v values are represented on one axis that runs out of the paper/screen. Briefly referring back to FIGS. 2a and 2b, positive values of y represent positions that may be located directly in front of the display 118, and negative values of y represent positions that are not located directly in front of the display 118. Briefly referring back to FIGS. 3b and 3d, positive values of v represent positions in the image that may correspond to locations that are directly in front of the display 118, and negative values of v represent positions in the image that do not correspond to locations that are directly in front of the display 118.

For example, a point that has a negative x value and a positive y value is located directly in front of the display 118 provided the x value and the y value do not exceed the dimensions of the display. Similarly, a point that has a positive u value and a positive v value represents a position in the image that corresponds to a location that is directly in front of the display 118 provided the u value and the v value do not represent values that exceed the dimensions of the display 118.

The z values are represented on one axis. The z-axis represents locations with reference to the surface of the display 118. Briefly referring back to FIGS. 2a and 2b, positive values of z represent positions that are located in front of (but not necessarily directly in front of) the display 118. Negative values of z represent positions that are located behind the display 118. A focal length, f, of the camera 107 is represented as a negative value positioned on the negative portion of the z-axis. The dimensions of the image constructed by the camera 107 correspond to the focal length of the camera 107.

The position of the projector 101 is represented as point p 404. Briefly referring back to FIG. 2a, the distance between the projector 101 and the camera 107 is represented by length b. A projection angle of the light emitted from the projector 101 relative to the display 118 is represented as the angle θ. The object location image point 316 of FIG. 3d is represented as point i 406, and has coordinate values $u_1$, $v_1$. The z-coordinate of point i 406 the focal length, f, of the camera 107.

The x, y, z-coordinate values of an object location point 408, represented as point o 408, which corresponds to the location of the user's finger 302, can be determined based on one or more of the following: the u-coordinate value of the object location image point 316 (e.g., $u_1$), the v-coordinate value of the object location image point 316 (e.g., $v_1$), the focal length of the camera 107 in pixels, and the distance between the projector 101 and the camera 107. In some example, the x, y, z-coordinate values of the object location point 408 can be determined according to the following equations:

$$x = \frac{b}{f*\cot(\theta) - u} * u$$

$$y = \frac{b}{f*\cot(\theta) - u} * v$$

$$z = \frac{b}{f*\cot(\theta) - u} * f$$

Once the x, y, z-coordinate values of the object location point 408 are determined, the control unit 105 determines whether the object location point 408 (which corresponds to the position of the user's finger 302 intersecting the plane 206) represents an invocation of a particular user interface element (e.g., a "press" of a button). In some examples, the control unit 105 compares the x, y, z-coordinate values of the object location point 408 to the x, y, z-coordinate values of user interface elements on the display 118 that are capable of being invoked. If the coordinate values of the object location point 408 fall within an area of a particular user interface element, the control unit 105 determines that the user is invoking the particular user interface element.

Figure 5:
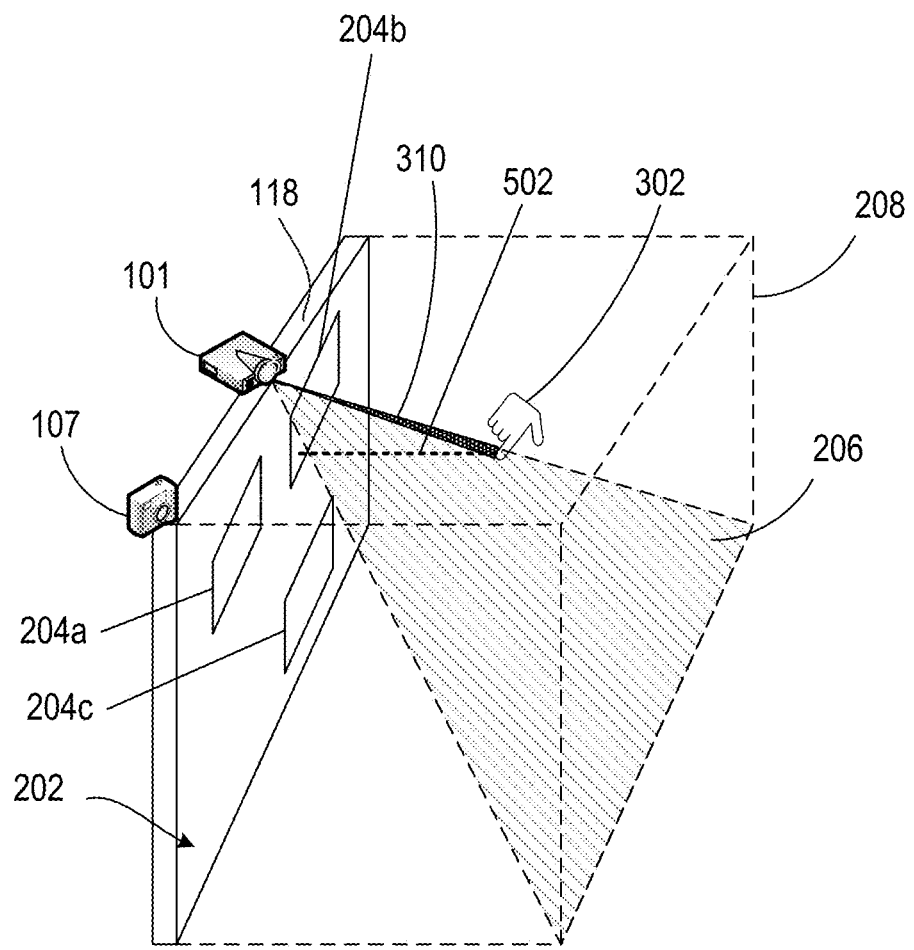
FIG. 5 is a perspective view of the display of FIGS. 3a and 3c in which the object is invoking a user interface element.

FIG. 5 shows a perspective view of the display 118 in which a particular user interface element 204b (e.g., a "stop blood pump" button) is invoked by the position of the user's finger 302. The control unit 105 determines the coordinate values that define the areas of the user interface elements 204a-c. The control unit 105 compares the x, y, z-coordinate value of the object location point (not shown) to the coordinate values that define the areas of the user interface elements 204a-c to determine whether the object location point is located within the area of one of the user interface elements 204a-c. In this example, the user's finger 302 is positioned at or close to the coordinate values of the object location point. The coordinate values of the object location point lie within the "stop blood pump" user interface element 204b, as represented by a line 502 that is perpendicular to the display 118 and aligned with the user's finger 302. The control unit 105 determines that the position of the user's finger 302 represents an invocation of the "stop blood pump" user interface element 204b. The control unit 105 may determine control data based on the processed input (e.g., the input received by the camera 107). In this example, the control unit 105 can determine control data that causes the hemodialysis machine 102 to stop the blood pump 132.

Figure 6A:
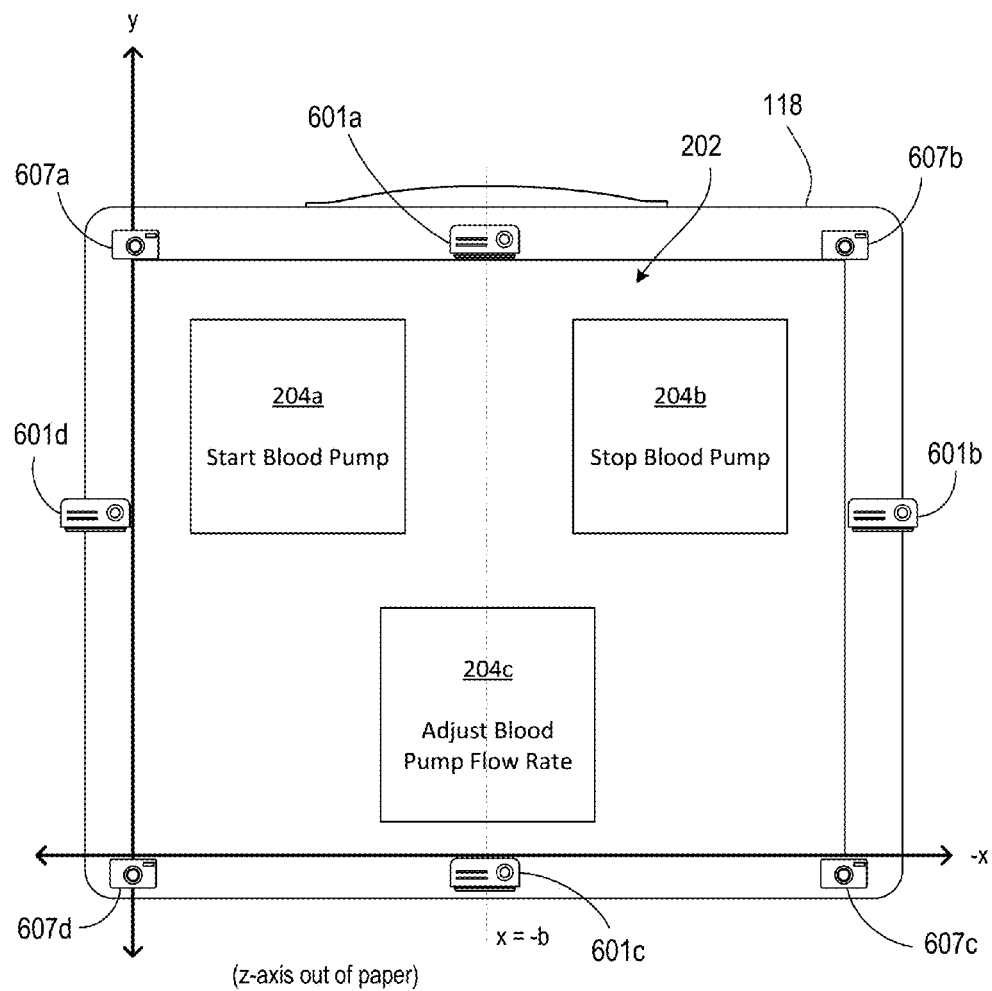
FIG. 6a is a front-facing view of the display of FIG. 1 in which the hemodialysis system includes multiple cameras and multiple projectors.
Figure 6B:
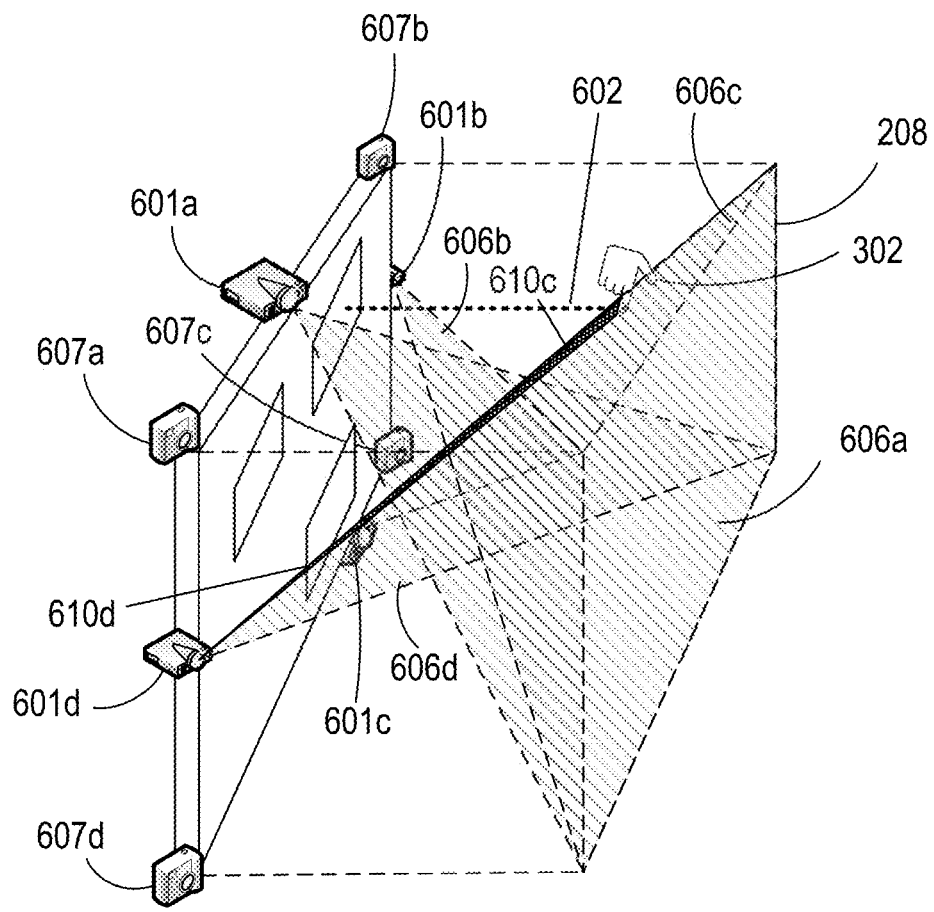
FIG. 6b is a perspective view of the display of FIG. 6a in which the object is invoking a user interface element.

FIGS. 6a and 6b show a front-facing view and a perspective view, respectively, of the display 118 in which the hemodialysis system 100 includes four projectors 601a-d and four cameras 607a-d. The projectors 601a-d are positioned at or near the middle of each edge of the display 118, and the cameras 607a-d are positioned at or near the corners of the display 118.

Each projector 601a-d emits infrared light in a respective plane 606a-d that runs through the space 208 in front of the display 118. As in the examples shown in the preceding figures, the first projector 601a emits light in a downwards diagonal manner in a particular plane 606a that runs from the top of the display 118 to the bottom of the space 208 in front of the display 118. The second projector 601b emits light in a sideways diagonal manner in a particular plane 606b that runs from the right side of the display 118 to the left side of the space 208 in front of the display 118. The third projector 601c emits light in an upwards diagonal manner in a particular plane 606c that runs from the bottom of the display 118 to the top of the space 208 in front of the display 118. The fourth projector 601d emits light in a sideways diagonal manner in a particular plane 606d that runs from the left side of the display 118 to the right side of the space 208 in front of the display 118. By having multiple projectors 601a-d, there is more area within the space 208 in front of the display 118 for the infrared light to be projected onto the object. Thus, it can be said that a hemodialysis system 100 with additional projectors has fewer "blind spots" (e.g., locations within the space 208 in front of the display 118 that do not intersect a plane of light emitted by a projector). Similarly, by having multiple cameras 607a-d, there is greater coverage of the space 208 in front of the display 118 for detecting the projected infrared light, further limiting potential blind spots.

As described above, each of the cameras 607a-d is configured to detect the infrared light that is projected onto the object and construct an image that include a representation of the infrared light. The representation of the infrared light appears as a segment of pixels in the constructed images. The control unit 105 (shown in FIG. 1) is configured to determine whether the object that is represented by the segment of pixels is an object of interest (e.g., a finger of the user 302), determine the u, v-coordinates of an object location image point in the constructed images based on the segment, determine the x, y, z-coordinate values of a point that corresponds to the location of the user's finger 302 within the space in front of the display 118 (e.g., the object location point), and determine whether the object location point represents an invocation of a particular user interface element (e.g., a "press" of a button).

As shown in FIG. 6b, the user's finger 302 intersects two planes—the plane 610c of infrared light emitted by the third projector 601c, and the plane 610d of infrared light emitted by the fourth projector 601d. The control unit 105 determines the coordinate values that define the areas of the user interface elements 204a-c, and compares the x, y, z-coordinate value of the object location point (not shown) to the coordinate values that define the areas of the user interface elements 204a-c to determine whether the object location point is located within the area of one of the user interface elements 204a-c. In this example, the object location point lies within the "stop blood pump" user interface element 204b, as represented by a line 602 that is perpendicular to the display 118 and aligned with the user's finger 302. The control unit 105 determines that the position of the user's finger 302 represents an invocation of the "stop blood pump" user interface element 204b.

In addition to reducing the number of blind spots within the space 208 in front of the display 118, the use of four projectors 601a-d and four cameras 607a-d may improve the accuracy of the system. In this example, because the user's finger 302 intersected two of the planes 610c, 610d of emitted infrared light, one or more of the images constructed by the cameras 607a-d may include a representation of the infrared light projected onto the user's finger 302 that has a different appearance than that of the segment 314 shown in FIG. 3d. For example, the image may include two segments, each segment corresponding to one of the planes 610c, 610d. Similarly, the u, v-coordinates of the object location image point may be determined based on the two segments (e.g., by averaging the coordinate values of each pixel of the two segments), thereby improving the accuracy of the determination.

In this example, one or more of the cameras 607a-d may have constructed an image that included a representation of the infrared light, and zero or more of the cameras 607a-d may have constructed an image that included no representation of the infrared light. In other words, zero or more of the cameras may have been unable to detect the infrared light projected onto the user's finger 302. In cases in which multiple cameras 607a-d construct an image that includes a representation of the infrared light, each of the corresponding images may be considered in determining the u, v-coordinates of the object location image point. For example, the u, v-coordinates of the object location image point may be determined by conflating information related to the segment(s) of the various images. In some implementations, the u, v-coordinates of each pixel of the segment(s) in a first image are averaged with the u, v-coordinates of each pixel of the segment(s) in a second image to determine the u, v-coordinates of the object location image point. In some implementations, coordinates related to one or more of the images undergo a conversion prior to the averaging to account for locational differences between the particular cameras 607a-d used to construct the images.

Figure 7:
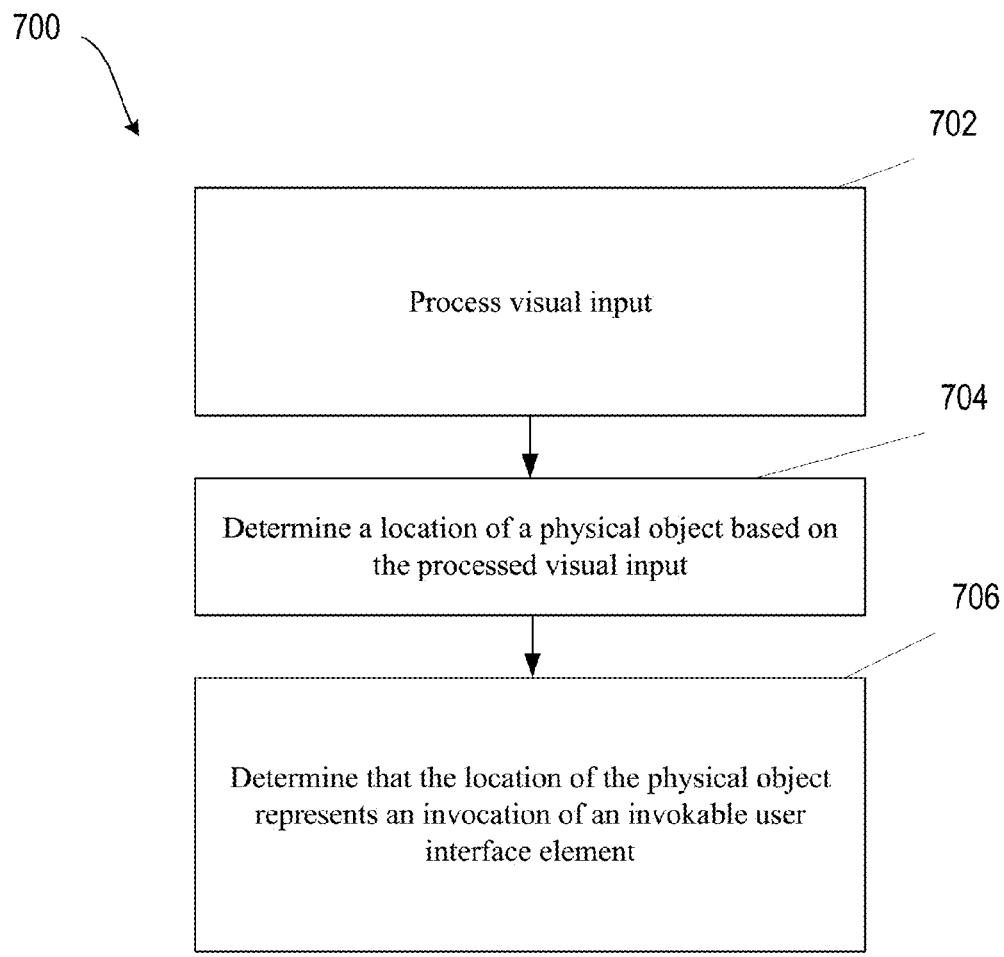
FIG. 7 is a flow chart illustrating a technique for determining an invocation of a user interface element.

FIG. 7 is a flowchart 700 illustrating a technique for determining, by a processor of a dialysis machine, an invocation of a user interface element displayed by the dialysis machine. Visual input is processed (702). The visual input may be received by a camera. A location of a physical object is determined based on the processed visual input (704). The visual input can include information related to a light that is projected onto the physical object. The light can be emitted by a projector. The light may be in the infrared range. The visual input may include an image of pixels. Each pixel can be defined by at least a u-coordinate value representing a horizontal position and a v-coordinate value representing a vertical position, and the position of the physical object can be determined based on the u-coordinate value and the v-coordinate value of a pixel of the image. The position of the physical object can be determined by calculating an x-coordinate value, a y-coordinate value, and a z-coordinate value, wherein the x, y, and z-coordinate values are each determined based on one or more of the following: the u-coordinate value, the v-coordinate value, the focal length, in pixels, of the camera, and the distance between the camera and the projector. Whether the physical object is a physical object of interest can be determined. The physical object may be determined to be a physical object of interested based at least in part on a width of the physical object. The physical object of interest may be a finger of a human hand. The light that is projected onto the physical object can be a line, and the length of the line can depend on the distance between a point in space and an origin of the projected light (e.g., the projector). The location of the physical object can be determined as representing an invocation of at least one invokable user interface element (706). The user interface element may be displayed by an electronic panel of the dialysis machine. The determination can be based on the processed visual input received on at least one occasion.

In some implementations, the display 118 is configured to receive multiple inputs from the user. The multiple inputs may be received at different times (e.g., a gesture), or may be concurrent (e.g., multi-gesture input). The capability to receive multiple inputs from the user increases the number of distinct interactions that the user can have with the display 118.

In some implementations, the user performs a gesture by moving an object (e.g., the user's finger) through the space 208 in front of the display 118. A first input may be received when the user's finger intersects the plane 206 at a first position, and a second input may be received when the user's finger moves to a second position that intersects the plane 206. Characteristics of the movement from the first position to the second position can determine the particular gesture that is being invoked. For example, the user may swipe his finger from the left to the right to cause the display 118 to present a previously-displayed screen (e.g., a "back" gesture), or the user may swipe his finger from the right to the left to cause the display 118 to present a next screen (e.g., a "next" gesture). Similarly, the user may swipe his finger from a top position to a bottom position to cause the display 118 to scroll down, or the user may swipe his finger from a bottom position to a top position to cause the display 118 to scroll up. In some implementations, the display 118 is configured to provide an indication when a gesture is detected. The visual indication may indicate the particular gesture that is detected.

In some implementations, the user performs a multi-gesture input by concurrently putting two object (e.g., a first and second finger of the user) in the space. In some implementations, one or both of the first finger and the second finger are moved through the space in a similar manner as described above. Characteristics of the positions and/or the movements of the fingers can determine the particular multi-gesture input that is being invoked. For example, the user may position his fingers in the space 208 in front of the display 118 such that each finger intersects the plane 206, and subsequently move his two fingers closer together (e.g., a pinch). The pinch may cause the display 118 to zoom out. Similarly, the user may position his fingers in the space 208 in front of the display 118 and subsequently move his two fingers further apart (e.g., a spread). The spread may cause the display 118 to zoom in. In some implementations, the display 118 is configured to provide an indication when a multi-gesture input is detected. The visual indication may indicate the particular multi-gesture input that is detected.

While certain implementations have been described, other implementations are possible.

While the hemodialysis system has been described as including a display with a non-contact interface, in some implementations, the hemodialysis system may include one or more additional input devices. In some implementations, the hemodialysis system includes a keyboard (e.g., a traditional push-button QWERTY keyboard). The one or more additional input devices may be used in place of the display (e.g., as an alternative input device for users who do not wish to use the non-contact interface of the display), or may be used in addition to the display (e.g., to input data in a manner that is not easily input using the non-contact interface of the display). In some implementations, in addition to having the non-contact interface, the display may also be a touchscreen that is capable of receiving touch inputs.

While the hemodialysis system has been described as including both a control unit and a panel control unit (e.g., two separate processors), in some implementations, the hemodialysis system includes a single control unit that is configured to perform the functions of both the control unit and the panel control unit. For example, the hemodialysis system can include a single processor that is configured to transmit control data for the hemodialysis machine, process input received by the camera, determine the location of the physical object in the field of view of the camera, and determine that the location of the physical objects represents an invocation of a particular user interface element.

In cases in which the hemodialysis system includes multiple cameras, if one of the cameras is obstructed, the hemodialysis system can use a different camera to carry out the functions described herein. Further, the use of multiple unobstructed cameras may provide additional locational data related to the physical object. The additional locational data may allow the hemodialysis system to determine the location of the physical object without knowing one or more other pieces of information described herein. For example, a hemodialysis system that includes multiple cameras may be able to determine the x, y, z-coordinate values of the object without knowing one or both of the focal length of the camera and the distance between the projector and the camera.

In cases in which the hemodialysis system includes multiple projectors, if one of the projectors is obstructed, the hemodialysis system can use a different projector to carry out the functions described herein. Further, as described above, the use of multiple unobstructed projectors may enable the non-contact interface of the display to detect physical objects more positions within the space in front of the display. For example, multiple unobstructed projectors can emit light in additional planes that run through the space in front of the display, thereby resulting in fewer blind spots, and in some examples, eliminating blind spots completely.

While the hemodialysis system has been described as including i) one projector and one camera and ii) four projectors and four cameras, the hemodialysis system can include other numbers of projectors and/or cameras. For example, in some implementations, the hemodialysis system includes two projectors and one camera. In some implementations, the hemodialysis system includes two projectors and two cameras. In some implementations, the hemodialysis system includes two projectors and four cameras. In some implementations, the hemodialysis system includes four projectors and one camera. In some implementations, the hemodialysis system includes four projectors and two cameras.

In some implementations, one of more of the cameras of the hemodialysis system may be oriented in ways other than described above. For example, one or more of the cameras may be oriented such that the camera is tilted toward the display. Such orientation may improve the ability for the camera to detect infrared light that is projected onto an object, thereby eliminating blind spots. In some implementations, adjusting the orientation of the camera may require different equations for determining the x, y, z-coordinate values of the object location point than those described above. For example, the particular angle of tilt of the camera may cause the constructed image to be warped (e.g., stretched), and such warping may call for different equations that factor in the angle of tilt to correct for the warping. In some implementations, a warped image constructed by a tilted camera may undergo preprocessing to correct the warping, thereby eliminating the need for different equations.

While the light emitted by the projector has been described as being an infrared light, the projector may emit other types of light. In some implementation, the projector emits another type of light that is not visible to the human eye. In some implementations, the projector emits a type of light that is visible to the human eye.

While the control unit has been described as determining an object location image point by averaging the coordinate values of each pixel in the segment of the image, other techniques may be employed. In some implementations, the control unit computes an average of the coordinate values of the endpoint pixels of the segment. In some implementations, the control unit computes the midpoint of the segment. In some implementations, a single object location image point is not determined, and instead, the coordinate values of the pixels of the segment are themselves used to represent the location of the object. In some implementations, the coordinate values of the pixels of the segment are processed in some other way to represent the location of the object.

While the invocation of a user interface element has been described as causing the dialysis machine to stop the blood pump, the techniques described herein can be used to cause the dialysis machine to perform one or more other actions in response to a user interface element being invoked. Such functions may or may not be related to dialysis.

While some specific examples of gestures and multi-gesture inputs have been described that can be received by the display, these examples are not exhaustive. In some implementations, the display is configured to receive one or more other gestures and multi-gesture inputs.

While the non-contact input device has been principally described as being part of a hemodialysis machine, the input device could alternatively be included in other types of medical treatment systems. Examples of other medical treatment systems in which the input device can be used include hemofiltration systems, hemodiafiltration systems, apheresis systems, cardiopulmonary bypass systems, and peritoneal dialysis systems.

Figure 8:
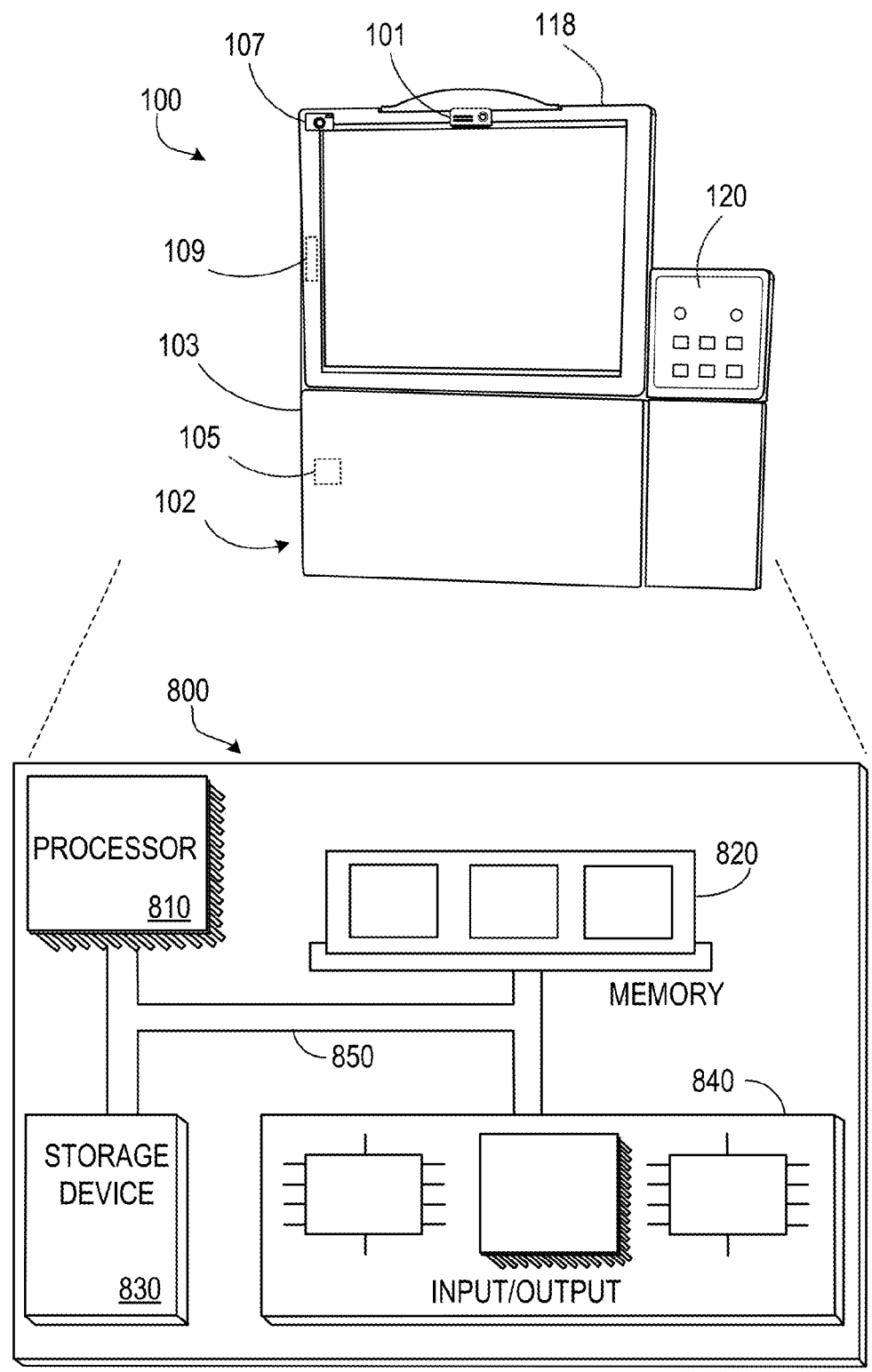
FIG. 8 is an example of a computer system and related components.

FIG. 8 is a block diagram of an example computer system 800. For example, referring to FIG. 1, the control unit 105, the panel control unit 109, or both (as separate units or as a single unit) could be examples of the system 800 described herein. In this example, the system 800 includes a processor 810, a memory 820, a storage device 830, and an input/output device 840. Each of the components 810, 820, 830, and 840 can be interconnected, for example, using a system bus 850. In some implementations, the control unit 105, the panel control unit 109, or both (as separate units or as a single unit) could be examples of the processor 810 (e.g., as oppose to the control unit 105 and/or the panel control unit 109 being examples of the entire system 800. The processor 810 is capable of processing instructions for execution within the system 800, as described in detail above. The processor 810 can be a single-threaded processor, a multi-threaded processor, or a quantum computer. The processor 810 can be capable of processing instructions stored in the memory 820, on the storage device 830, or both. The processor 810 may execute operations such as those described in detail above with respect to the control unit 105 and the panel control unit 109.

The memory 820 stores information within the system 800. In some implementations, the memory 820 is a computer-readable medium. The memory 820 can, for example, be a volatile memory unit or a non-volatile memory unit.

The storage device 830 is capable of providing mass storage for the system 800. In some implementations, the storage device 830 is a non-transitory computer-readable medium. The storage device 830 can include, for example, a hard disk device, an optical disk device, a solid-date drive, a flash drive, magnetic tape, or some other large capacity storage device. The storage device 830 may alternatively be a cloud storage device, e.g., a logical storage device including multiple physical storage devices distributed on a network and accessed using a network.

The input/output device 840 provides input/output operations for the system 800. In some implementations, the input/output device 840 includes one or more of network interface devices (e.g., an Ethernet card), a serial communication device (e.g., an RS-232 10 port), and/or a wireless interface device (e.g., an 802.11 card, a 3G wireless modem, or a 4G wireless modem). A network interface device allows the system 800 to communicate (e.g., transmit and receive data) with other devices. In some implementations, the input/output device 840 includes driver devices configured to receive input data and send output data to other input/output devices (e.g., the display 118, the control panel 120, a keyboard, and/or a printer, among others). In some implementations, mobile computing devices, mobile communication devices, and other devices are used. The system described herein may be used with any one or more of, including combinations of, appropriate wireless communication technologies, such as cellular or mobile network technologies, WiFi technologies, and/or other short distance wireless communication technologies, including Bluetooth and/or near field communication (NFC). The wireless communications may involve appropriate security and encryption protocols or standards, and may be used in conjunction with appropriate wireless hardware and software components that support such wireless communication technologies.

While an example computer system 800 has been described with reference to FIG. 8, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification, such as software for determining an invocation of a user interface element displayed by a dialysis machine (e.g., as described with reference to FIG. 6), can be implemented as one or more computer program products, (e.g., one or more modules of computer program instructions encoded on a tangible program carrier), such as a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "computer system" may encompass all apparatus, devices, and machines for processing data, including by way of example a programmable processor, a computer, or multiple processors or computers. A processing system can include, in addition to hardware, code that creates an execution environment for the computer program in question (e.g., code that constitutes processor firmware), a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of nonvolatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

A number of implementations have been described. Nevertheless, it will be understood that various modifications may be made without departing from the spirit and scope of the invention. Accordingly, other implementations are within the scope of the following claims.

What is claimed is:

1. A dialysis machine comprising:
  one or more processing units configured to transmit control data;
  a pump configured to pump medical fluid to and from a patient based at least in part on control data received from the processing unit;
  an electronic panel comprising:
    a display surface, and
    at least one panel control unit configured to cause the electronic panel to display at least one user interface element that can be invoked by a user;
  at least one projector configured to emit light; and
  at least one camera configured to detect the emitted light;
  wherein the one or more processing units are configured to:
    process input received by the camera,
    determine a location of a physical object in a field of view of the camera based on the processed input, including:
      identifying a segment of light projected onto the physical object by the projector;
      constructing an image that includes a representation of the segment of light, the representation comprising a plurality of pixels each having coordinates in the image, wherein each pixel is defined by at least a u-coordinate value representing a horizontal position in the image and a v-coordinate value representing a vertical position in the image;
      averaging the coordinates of the plurality of pixels to determine a location of the physical object in the image; and
      determining the location of the physical object in the field of view of the camera based on the determined location of the physical object in the image, comprising calculating an x-coordinate value, a y-coordinate value, and a z-coordinate value of the physical object, wherein the x, y, and z-coordinate values are each determined based on one or more of the following: one or more of the u-coordinate values, one or more of the v-coordinate values, a focal length of the camera in pixels, and a distance between the projector and the camera;
    determine that a width of the physical object is less than a predetermined threshold,
    determine, based on the determined location of the physical object in the field of view of the camera and the determination that the width of the physical object is less than the predetermined threshold, that the determined location of the physical object represents an invocation of the at least one user interface element displayed on the electronic panel, and
    determine the control data based on the processed input.

2. The dialysis machine of claim 1, wherein the at least one processor is configured to determine that the physical object is a physical object of interest.

3. The dialysis machine of claim 2, wherein the physical object is determined to be a physical object of interest based at least in part on the width of the physical object.

4. The dialysis machine of claim 2, wherein the physical object of interest is a finger of a human hand.

5. The dialysis machine of claim 1, wherein the projector emits a line of light, wherein the length of the line depends on a distance between a point in space and the projector.

6. The dialysis machine of claim 1 comprising four projectors and four cameras, wherein a first projector is positioned above the electronic panel, a second projector is positioned below the electronic panel, a third projector is positioned to a left side of the electronic panel, and a fourth projector is positioned to a right side of the electronic panel.

7. A method performed by one or more processors of a dialysis machine, the method comprising:
  processing visual input;
  determining a location of a physical object in a field of view based on the processed visual input, including:
    identifying a segment of light projected onto the physical object;
    constructing an image that includes a representation of the segment of light, the representation comprising a plurality of pixels each having coordinates in the image, wherein each pixel is defined by at least a u-coordinate value representing a horizontal position in the image and a v-coordinate value representing a vertical position in the image;

averaging the coordinates of the plurality of pixels to
determine a location of the physical object in the
image; and determining the location of the physical object in the
field of view based on the determined location of the
physical object in the image, comprising calculating
an x-coordinate value, a y-coordinate value, and a
z-coordinate value of the physical object, wherein
the x, y, and z-coordinate values are each determined
based on one or more of the following: one or more
of the u-coordinate values, one or more of the
v-coordinate values, a focal length of the camera in
pixels, and a distance between the projector and the
camera;

determining that a width of the physical object is less than
a predetermined threshold; and determining, based on the determined location of the
physical object in the field of view and the determination that the width of the physical object is less than the
predetermined threshold, that the determined location
of the physical object represents an invocation of at
least one invokable user interface element displayed by
an electronic panel of the dialysis machine.

8. The method of claim 7, wherein the visual input includes information related to the segment of light that is projected onto the physical object.

9. The method of claim 7, wherein the light comprises infrared light.

10. The method of claim 7 comprising determining that the physical object is a physical object of interest.

11. The method of claim 10, wherein the physical object is determined to be a physical object of interest based at least in part on the width of the physical object.

12. The method of claim 10, wherein the physical object of interest is a finger of a human hand.

13. At least one non-transitory computer-readable medium storing instructions operable to cause one or more computer to perform operations comprising:

processing visual input;

determining a location of a physical object in a field of view based on the processed visual input, including;

identifying a segment of light projected onto the physical object;

constructing an image that includes a representation of the segment of light, the representation comprising a plurality of pixels each having coordinates in the image, wherein each pixel is defined by at least a u-coordinate value representing a horizontal position in the image and a v-coordinate value representing a vertical position in the image;

averaging the coordinates of the plurality of pixels to determine a location of the physical object in the image; and determining the location of the physical object in the field of view based on the determined location of the physical object in the image, comprising calculating an x-coordinate value, a y-coordinate value, and a z-coordinate value of the physical object, wherein the x, y, and z-coordinate values are each determined based on one or more of the following: one or more of the u-coordinate values, one or more of the v-coordinate values, a focal length of the camera in pixels, and a distance between the projector and the camera;

determining that a width of the physical object is less than a predetermined threshold; and determining, based on the determined location of the physical object in the field of view and the determination that the width of the physical object is less than the predetermined threshold, that the determined location of the physical object represents an invocation of at least one invokable user interface element displayed by an electronic panel of a dialysis machine.

* * * * *